Figure 1:
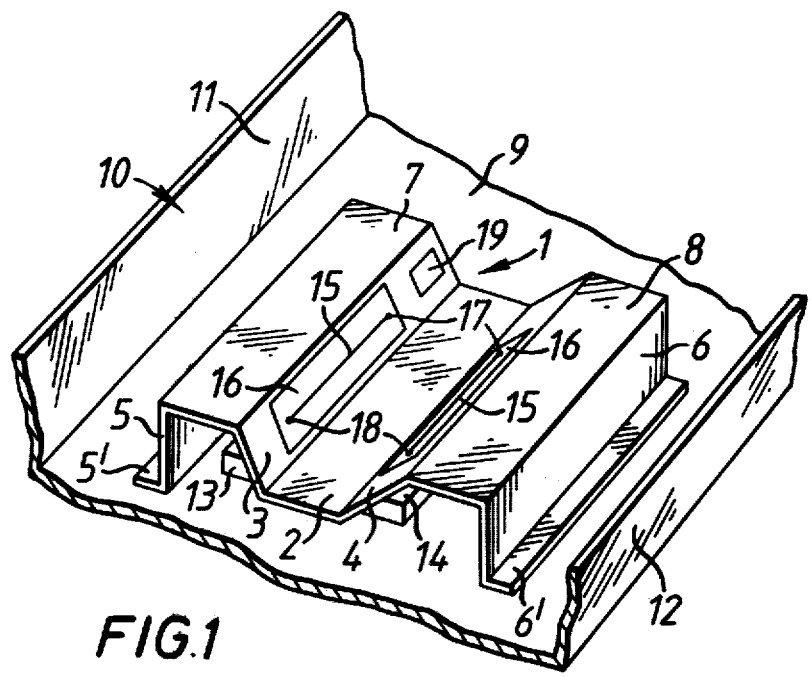

United States Patent [19]

Hewitt et al.

[11] 4,311,957
[45] Jan. 19, 1982

[54] MEASUREMENT OF MOISTURE CONTENT

[75] Inventors: Sidney J. Hewitt, West Wellow; Juan M. Ozamiz, Romsey; Albert E. Yallup, Totton, all of England

[73] Assignee: British-American Tobacco Company Limited, London, England

[21] Appl. No.: 135,292

[22] Filed: Mar. 31, 1980

[51] Int. Cl.³ .............................. G01R 27/04
[52] U.S. Cl. ........................... 324/58.5 R; 324/61 R
[58] Field of Search .............. 324/58.5 R, 58.5 A, 324/58.5 B, 58 R, 61 R

[56] References Cited

U.S. PATENT DOCUMENTS

| 3,430,139 | 2/1969 | Schluter | 324/58.5 A |
| 3,811,087 | 5/1974 | Schmeizer | 324/58.5 A |
| 3,913,012 | 10/1975 | Kujath | 324/58.5 A |
| 3,956,695 | 5/1976 | Stamm | 324/58.5 A |
| 4,123,702 | 10/1978 | Kinanen | 324/58.5 A |

FOREIGN PATENT DOCUMENTS 1139204  11/1962  Fed. Rep. of Germany .... 324/58 R

Primary Examiner—Stanley T. Krawczewicz
Attorney, Agent, or Firm—Kane, Dalsimer, Kane, Sullivan and Kurucz

[57] ABSTRACT

Apparatus and method for measuring the moisture content of a material, particularly a tobacco material, in which a microwave signal is divided between first and second signal paths, said first path comprising a sampling capacitor, the dielectric of which comprises the said material, and said second path comprising reference delay means, signals from each of the paths being fed to a phase detector providing an output indicative of waveform time displacement of one of said signals relative to the other of said signals. Advantageously signals from each of the said paths are fed through substantially identical first and second limiting amplifiers directly to the said phase detector. A second microwave signal of a frequency different from, but close to, that of the first-named microwave signal may be mixed with the signals from the sampling capacitor and from the reference delay means, the resultant beat signals of lower frequency being fed to the phase detector.

9 Claims, 2 Drawing Figures

MEASUREMENT OF MOISTURE CONTENT

This invention relates to the measurement of the moisture content of fibrous, filamentary or particulate material, especially but not exclusively the aqueous moisture content of tobacco.

Apparatus intended for the moisture measurement of a moving stream of tobacco is disclosed in United Kingdom Patent Specification No. 994,445 and comprises a vibratory conveyor having a centrally disposed measuring channel of V-section in which capacitor plates are so mounted as to contact cut tobacco fed along the measuring channel. In operation of this known apparatus a voltage field is established between the capacitor plates and a signal emanating from associated electrical circuitry is utilised as an indicator of the moisture content of the cut tobacco.

When a high frequency beam of energy is passed through a material, a determination may be made of the moisture content of the material by measuring either the dielectric constant of the material or the attenuation of the energy of the beam which results by passage of the beam through the material. It is known to employ radio frequency radiation when the measurement of dielectric constant is used, but although the method, when employed for measuring the moisture content of tobacco, is reliable for moisture contents up to about 30%, the reliability falls off sharply thereafter. The energy attenuation method has been used at microwave frequencies, but again reliability sharply decreases at about 30% moisture content for tobacco.

The present invention seeks to extend the range of possible reliable moisture-content determination and, in particular, to provide a relatively accurate and convenient apparatus and method for measuring moisture contents of tobacco of up to 40% or more. Such an extension of the range of reliable measurement is of practical significance in the tobacco industry if requirements arising with different tobacco constituents, lamina and stem, reconstituted tobacco and tobacco-substitute constituents, are to be satisfied.

The present invention provides a moisture content measuring apparatus comprising a microwave signal generator, first and second signal paths, a signal divider operable to divide a microwave signal from said generator between said first and second paths, a sampling capacitor in said first path arranged to receive fibrous, filamentary or particulate material which provides a dielectric, reference delay means in said second path, and a phase detector arranged to receive signals from said first and second paths and to provide an output indicative of the waveform time displacement of said signals.

The present invention further provides a method of measuring the moisture content of the material, particularly tobacco, wherein a microwave signal is divided between first and second signal paths, said first path comprising a sampling capacitor the dielectric of which comprises the material, and said second path comprising reference delay means, signals from each of the paths being fed to a phase detector providing an output indicative of waveform time displacement of one of said signals relative to the other of said signals. The method has particular advantage where the material is tobacco, but is applicable also to other materials such as paper-sheet materials and materials comprising small particles of the size of flour, for example cement materials.

Advantageously, the microwave signal fed to the first and second paths is divided equally between the said paths and substantially identical limiting amplifiers are arranged in the respective paths to feed signals directly to the phase detector. It is preferable to mix a second microwave signal, of a frequency different from but close to that of the first-mentioned signal, with the signals emanating respectively from the sampling capacitor and the reference delay means, so that beat signals fed to the phase detector are of a considerably lower frequency, for example 100 MHz where the microwave signal has a frequency of the order of 1.2 GHz.

The present invention finds useful application in the measurement or continuous monitoring of the moisture content of a moving stream of cut tobacco. In this regard it may be noted that the sampling capacitor should be of such form as to ensure a constant density of the tobacco stream in the region of the sampling capacitor because substantial variations in tobacco density would give rise to errors in the output signal from the phase detector. With this object in view, the tobacco stream may be confined within a closed duct. Alternatively, if an open channel is used, it may be arranged that the tobacco stream flowing therethrough is maintained at a constant depth. In the case of the arrangement disclosed in Specification No. 994,445, the open measuring channel is maintained full of tobacco, surplus tobacco being shed at each side of the channel to receiving means.

Figure 2:
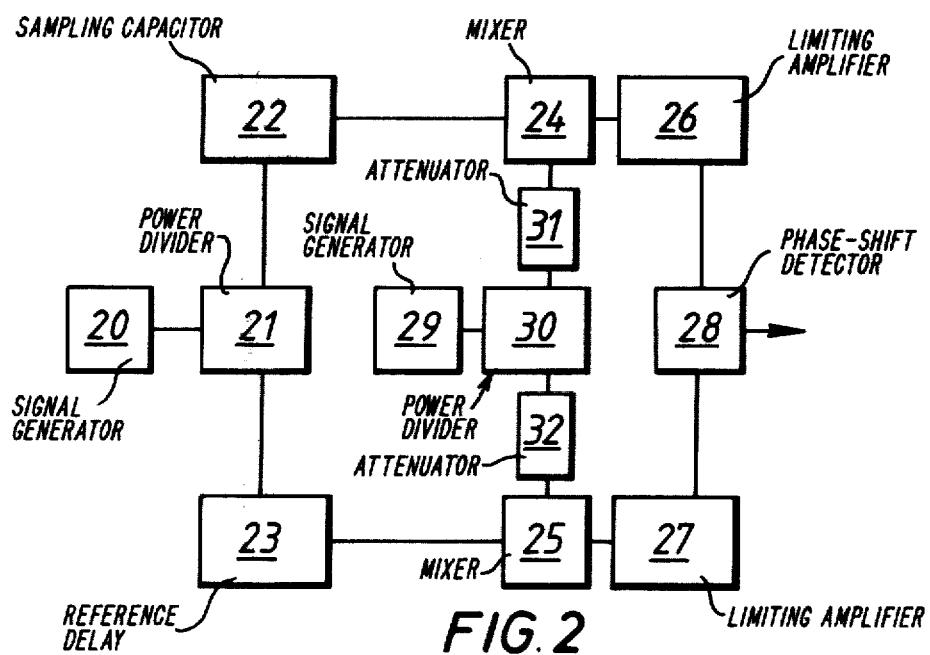

In order that the invention may be clearly understood and readily carried into effect, reference will now be made, by way of example, to the accompanying drawings, in which:

FIG. 1 shows apparatus for measuring the moisture content of a moving stream of tobacco; and FIG. 2 shows a block diagram illustrating schematically circuitry forming part of the apparatus of FIG. 1.

Referring to FIG. 1, the apparatus shown comprises a sheet-metal channel unit 1 of which a central portion constitutes a measuring channel, for example with a depth of 65 mm, defined by a bottom wall 2 and upward sloping, upwardly divergent, side walls 3 and 4. The channel unit 1 is formed to provide vertical support walls 5 and 6 and lands 7 and 8 interconnecting respectively the walls 3 and 4 and the walls 5 and 6 of the measuring channel. The walls 5 and 6 are provided with out-turned foot portions $5^1$, $6^1$ respectively by which channel unit 1 is mounted upon and firmly secured to the upper surface of the bottom wall 9 of a downwardly sloping vibratory conveyor 10, the said unit being disposed equidistantly from respective side walls 11 and 12 of the conveyor 10. As may be seen from FIG. 1, the bottom wall 2 of the measuring channel of the channel unit 1 is disposed at a distance, suitably 60 mm, above the bottom wall 9 of the conveyor 10. There is secured to the under surface of the wall 2 a box 13 housing microwave circuitry to be described with reference to FIG. 2.

In use of the moisture-measuring apparatus, tobacco is fed to the measuring channel 2, 3, 4 at such a rate as to maintain the channel full, surplus tobacco spilling over into the conveyor 10. Thus the density of the tobacco passing along the measuring channel is substantially constant.

Set into the side walls 3, 4 of the measuring channel are parts of a two-part planar transmission line, each in the form of a straight microstrip 15 which is embedded in a dielectric substrate 16 backed by a grounded plate (not shown). Each substrate 16 is received in a rectangular opening in a respective wall 3, 4, the upper surface of each substrate being flush with the upper surface of the respective said wall. The ends 17 of the microstrips are connected to microwave components within the box 13, while the other ends 18 are interconnected by a conductor (not shown) disposed exteriorly of the measuring channel, so that the two parts of the transmission line are in series.

In an alternative arrangement (not shown), use may be made of a one-part planar transmission line set into the upper wall 14 of the box 13 and comprising a microstrip of symmetrical meander configuration which is embedded in a dielectric substrate backed by a grounded plate. The substrate is received in a rectangular opening in the bottom wall 2 of the channel, the upper surface of the substrate being flush with the upper surface 14 of that wall. The ends of the microstrip are connected to the microwave components within the box 13.

Microwave dielectric materials suitable for forming the substrates 16 or substrate have a relative dielectric constant of about 2.1 to 2.6 and may be polyolefins, for example polypropylene or high-density polyethylene.

A temperature measuring probe 19 is set into the side wall 3 of the measuring channel.

The circuitry schematically illustrated in FIG. 2 comprises a microwave signal generator 20 operable to generate a signal of circa 1.2 GHz. The signal propagated by the generator 20 passes to an in-phase power divider 21 which functions to provide equally divided, in-phase, signals to each of two parallel signal paths.

Connected in the first of these signal paths is the transmission line of which the microstrips 15, together with the dielectric substrates 16 and adjacent portions of the walls 2, 3 of the measuring channel constitute a sampling capacitor (designated 22 in FIG. 2). The arrangement is such that, in operation of the apparatus, the microwave signal transmitted along the line 15, 15 travels partly within the tobacco in the measuring channel.

The second of the signal paths comprises a fixed reference delay 23 in the form of a stripline (not shown) of approximately the same electrical length as the microstrip line 15, 15.

The first and second signal paths further include identical mixers 24, 25 and identical limiting amplifiers 26, 27. A voltage phase shift detector 28 is arranged to receive signals from the amplifiers 26, 27 and to provide a d.c. output signal.

The microwave circuitry of FIG. 2 further includes a second microwave signal generator 29, operable in this case to generate a signal of circa 1.1 GHz. The signal propagated by the generator 29 passes to an in-phase power divider 30 which functions to provide equally divided, in-phase, output signals. These output signals are fed, via respective identical attenuators 31 and 32, to the mixers 24 and 25. Thus the signals received by the limiting amplifiers 26 and 27 instead of being microwave signals, are beat signals having frequencies of the order of 100 MHz.

The above described microwave components are interconnected by semi-rigid microwave cables and all of these components and cables are mounted in the box 13. This is an advantageous arrangement since if, alternatively, a microwave transmission cable extended from a component within the box 13 to an external component mounted stationarily relative to the vibratory conveyor 10, the resultant flexing of the cable would give rise to errors in the phase shift measured by the detector 28.

The only connections made to the circuitry in the box 13 are for D.C. power supplies for the signal generators 20 and 29, and for output d.c. signals. One of the d.c. signals is the output signal from the phase-shift detector 28, which signal is fed to a voltmeter (not shown).

It has been determined that for tobacco moisture contents of up to about 43% changes in the moisture content produce proportional changes in the dielectric constant (at microwave frequencies) of the sampling capacitor 22. Since the phase shifts detected by the detector 28 are proportional to changes in the dielectric constant at the sampling capacitor 22, the former changes are proportional to the moisture content changes. Thus the voltmeter receiving the output signal of the phase detector 28 can be directly calibrated in % moisture units. The purpose of including the reference delay 23 in the second signal path is to ensure that the time phase shift present at the detector 28 is measurable on the straight portions of the voltage waveforms.

Phase shift errors due to variations in signal-voltage level or because of variations in signal power from the signal generator 20 are eliminated by use of the limiting amplifiers 26 and 27. The symmetry of the circuitry of FIG. 2 eliminates phase-measurement errors which would otherwise result from circuit temperature changes. Temperature changes of the tobacco are detected by the probe 19 and the signal therefrom is utilized by means (not shown), for example a Wheatstone-bridge circuit balanced at a preselected mean temperature, to apply a compensatory adjustment to the output signal from the phase detector 28.

Although a signal with a frequency in the region of 1 GHz gives good results and permits the use of comparatively inexpensive components, it will be appreciated that higher microwave frequencies could be employed.

What we claim is:

1. Apparatus for the continuous measurement of the moisture content of a loose fibrous, filamentary or particulate material, comprising a microwave signal generator, first and second signal paths, a signal divider operable to divide a microwave signal from said generator between said first and second paths, a sampling capacitor in said first path arranged to receive the said material which provides a dielectric, reference delay means in said second path, and a phase detector arranged to receive signals from said first and second paths and to provide an output indicative of the waveform time displacement of said signals.

2. Apparatus according to claim 1, comprising also first and second substantially identical limiting amplifiers, arranged in said first and second paths respectively to feed signals directly to said phase detector.

3. Apparatus according to claim 1 or 2, comprising also a second generator, producing a second microwave signal of a frequency different from but close to that of the microwave signal produced by the first-named generator, means for mixing the said second microwave signal with signals emanating from the sampling capacitor and from the reference delay means, and means for feeding beat signals produced by the mixing means to the phase detector.

4. A method for the continuous measurement of the moisture content of a loose fibrous, filamentary or particulate material, wherein a microwave signal is divided between first and second signal paths, said first path comprising a sampling capacitor the dielectric of which comprises the said material, and said second path comprising reference delay means, signals from each of the paths being fed to a phase detector providing an output indicative of waveform time displacement of one of said signals relative to the other of said signals.

5. A method according to claim 4, wherein said signals from each of the said paths are fed through substantially identical first and second limiting amplifiers respectively directly to the said phase detector.

6. A method according to claim 4 or 5, wherein the said material is tobacco material.

7. A method according to claim 4 or 5, wherein the microwave signal fed to the first and second paths is divided equally between the said paths.

8. A method according to claim 4 or 5, wherein a second microwave signal of a frequency different from, but close to, that of the first-named microwave signal is mixed with the signals emanating from the sampling capacitor and from the reference delay means, the resultant beat signals of considerably lower frequency than the microwave signals being fed to the phase detector.

9. A method according to claim 4 or 5, wherein the material is maintained at a constant density in the region of the sampling capacitor by maintaining constant the depth of the tobacco stream in an open channel.

* * * * *